US011174951B2

(12) United States Patent
Chuo et al.

(10) Patent No.: US 11,174,951 B2
(45) Date of Patent: Nov. 16, 2021

(54) BALL VALVE FOR FERMENTATION TANK AND FERMENTATION TANK INCLUDING THE SAME

(71) Applicants:Chin-Hsing Chuo, Taichung (TW); Chih-Meng Wang, Taichung (TW); Chin-Yen Wang, Taichung (TW)

(72) Inventors: Chin-Hsing Chuo, Taichung (TW); Chih-Meng Wang, Taichung (TW); Chin-Yen Wang, Taichung (TW)

( * ) Notice: Subject to any disclaimer, the term of this patent is extended or adjusted under 35 U.S.C. 154(b) by 232 days.

(21) Appl. No.: 16/347,784

(22) PCT Filed: Dec. 9, 2016

(86) PCT No.: PCT/CN2016/109127
§ 371 (c)(1),
(2) Date: May 6, 2019

(87) PCT Pub. No.: WO2018/103056
PCT Pub. Date: Jun. 14, 2018

(65) Prior Publication Data
US 2019/0353256 A1    Nov. 21, 2019

(51) Int. Cl.
*F16K 5/06* (2006.01)
*F16K 27/06* (2006.01)
*C12M 1/00* (2006.01)

(52) U.S. Cl.
CPC ............ *F16K 5/0605* (2013.01); *C12M 29/00* (2013.01); *C12M 39/00* (2013.01); *F16K 5/06* (2013.01);
(Continued)

(58) Field of Classification Search
CPC ........ F16K 5/0605; F16K 5/06; F16K 27/067; C12M 29/00; C12M 39/00;
(Continued)

(56) References Cited

U.S. PATENT DOCUMENTS 3,464,449 A * 9/1969 Morton ................... F16K 24/02
                                                            137/625.24
3,605,789 A * 9/1971 Graham ................... F16K 5/205
                                                            137/240

(Continued)

FOREIGN PATENT DOCUMENTS

CA            2145119            9/1995
CN        201386821 Y  *       1/2010
(Continued)

*Primary Examiner* — David Colon-Morales
(74) *Attorney, Agent, or Firm* — Muncy, Geissler, Olds & Lowe, P.C.

(57) ABSTRACT

A ball valve for fermentation tank includes a main body, a ball body, and a rotation mechanism. The main body encloses a chamber therein and has a first inlet, a first outlet, and a discharge port therebetween. The ball body has a flow channel with a second inlet, a second outlet, and a liquid intake port. A gap is formed between the ball body and the main body. The rotation mechanism is connected to the ball body to make it rotate. When the ball body is at an open position, the second inlet communicates the first inlet, the second outlet communicates the first outlet, and the liquid intake port communicates the gap. When the ball body is at a washing position, the second inlet and the second outlet face the gap, the liquid intake port communicates the first inlet.

6 Claims, 7 Drawing Sheets

(52) U.S. Cl.
CPC ......... *F16K 27/067* (2013.01); *Y10T 137/043* (2015.04)

(58) Field of Classification Search
CPC ......... Y10T 137/0402; Y10T 137/0419; Y10T 137/0424; Y10T 137/043
See application file for complete search history.

(56) References Cited

U.S. PATENT DOCUMENTS

| | | | | |
|---|---|---|---|---|
| 4,749,002 A * | 6/1988 | Lembser | ................ | F16K 5/20 137/246.22 |
| 4,965,051 A * | 10/1990 | Shukunobe | ............ | C12M 23/34 134/166 R |
| 5,113,895 A * | 5/1992 | Le Devehat | .............. | F16K 5/06 137/244 |
| 5,467,796 A * | 11/1995 | Pettinaroli | ............ | F16K 5/0605 134/166 C |
| 5,632,294 A * | 5/1997 | Benton | ................ | F16K 5/0605 137/1 |
| 5,842,683 A | 12/1998 | Wei | | |
| 6,161,582 A * | 12/2000 | Asano | ................ | F16K 5/0605 137/625.21 |
| 6,189,522 B1 * | 2/2001 | Moriya | ................ | F02P 15/08 123/643 |
| 6,435,474 B1 | 8/2002 | Williams et al. | | |
| 6,540,206 B2 * | 4/2003 | Guerra | ................ | F16K 5/0605 137/270 |
| 6,578,598 B2 * | 6/2003 | Gardner | ................ | F16K 5/0605 137/240 |
| 6,681,802 B2 * | 1/2004 | McHugh | ............. | F16K 11/0873 137/559 |
| 6,832,621 B1 * | 12/2004 | Williams | ................ | B08B 9/00 134/166 C |
| 7,089,960 B2 * | 8/2006 | Maruta | ................ | F16K 5/0605 137/625.22 |
| 8,316,886 B2 * | 11/2012 | Olsen | .................... | F24D 3/1058 137/597 |
| 8,375,977 B2 | 2/2013 | Jones | | |
| 8,752,570 B2 * | 6/2014 | Donahue | ................ | F16K 15/031 137/68.23 |
| 8,881,767 B2 * | 11/2014 | Bartell | ............... | F16K 11/0873 137/625.32 |
| 9,322,749 B2 * | 4/2016 | Newbold | ................ | C12M 37/00 |
| 9,696,244 B2 * | 7/2017 | Carter | ................ | F16K 11/076 |
| 10,160,947 B2 * | 12/2018 | Bourdat | ................ | G01N 1/286 |
| 2010/0252129 A1 * | 10/2010 | Olsen | ................ | F16K 24/02 137/597 |

FOREIGN PATENT DOCUMENTS

| | | |
|---|---|---|
| CN | 203963100 U | 11/2014 |
| CN | 205207756 U | 5/2016 |

\* cited by examiner

BALL VALVE FOR FERMENTATION TANK AND FERMENTATION TANK INCLUDING THE SAME

BACKGROUND OF THE INVENTION

Field of the Invention

The present invention relates to a ball valve for fermentation tank and a fermentation tank including the ball valve.

Description of the Prior Art

Generally, the outlet of the fermentation tank is disposed with a valve to control the discharging of the product. Ball valve is often used here. Specifically, the ball valve includes a main body, a ball body, and a rotation mechanism. The ball body is disposed in the main body and is rotatable by the rotation mechanism. The ball body has a flow channel. When the flow channel communicates the outlet of the fermentation tank, the product can be discharged. When the flow channel doesn't communicate the outlet, the product is not discharged.

However, the product of fermentation is not only liquid but also solid residue. The residue may be brought into the gap between the main body and the ball body when the ball body is rotated to spoil. Thus, the product passing through may by contaminated.

Besides, the fermentation tank has to be washed and sterilized after process of fermentation. The ball valve has to be kept opened to discharge the waste water. Thus, detergent is unable to enter the gap between the ball body and the main body for cleaning.

To clean the ball valve thoroughly, the ball valve has to be detached and dismantled. Thus, the process of fermentation can not go on continuously.

SUMMARY OF THE INVENTION

The main object of the present invention is to provide a ball valve for fermentation tank which is able to be washed without being removed from the fermentation tank.

To achieve the above and other objects, the ball valve for fermentation tank includes a main body, a ball body, and a rotation mechanism.

The main body encloses a chamber therein. The main body has a first inlet and a first outlet at two ends thereof. The first inlet and the first outlet communicate the chamber respectively. The main body has a discharge port on a lateral wall thereof. The discharge port communicates the chamber and is located between the first inlet and the first outlet. A first valve is disposed on the discharge port. The ball body is rotatably received in the chamber of the main body. The ball body is formed with a flow channel. Two ends of the flow channel are a second inlet and a second outlet respectfully. The ball body further has a liquid intake port communicating the flow channel. A gap is formed between the ball body and an inner wall of the chamber. The rotation mechanism is connected to the ball body to make the ball body rotate between an open position and a washing position. When the ball body is located at the open position, the second inlet communicates the first inlet, the second outlet communicates the first outlet, and the liquid intake port faces the gap to communicate the gap. When the ball body is located at the washing position, the second inlet and the second outlet both face the gap, and the liquid intake port communicates the first inlet.

To achieve the above and other objects, a fermentation tank of the present invention includes the ball valve mentioned above and further includes a tank body. The tank body has an inlet and an outlet. The ball valve is disposed on the inlet. The first inlet is connected to the inlet of the tank body.

Thereby, the ball valve provides raw material filling mode, fermentation tank and ball valve washing mode, and ball valve washing mode to use. Residue is prevented from accumulating inside the ball valve, and it's not necessary to remove the ball valve from the fermentation tank for cleaning. In addition, the waste water after washing can be discharged via the discharge port and may not contaminate the fermentation tank.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
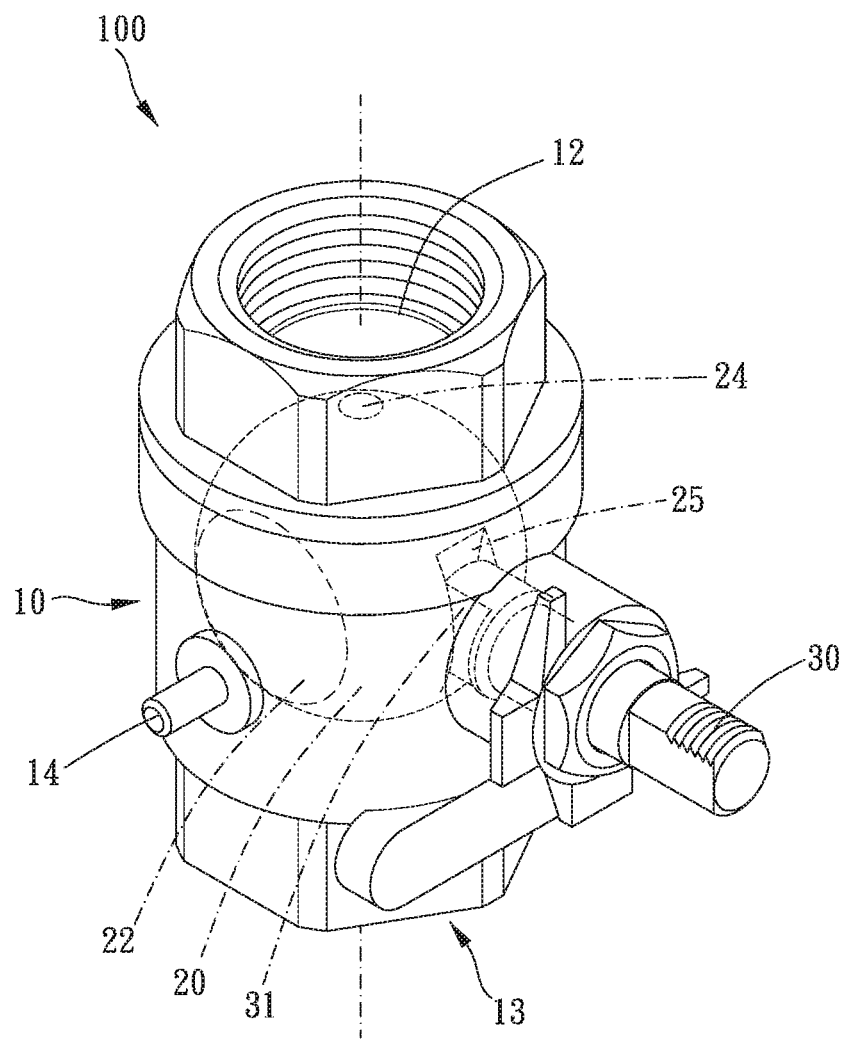
FIG. 1 is a stereogram of a ball valve of the present invention.
Figure 2:
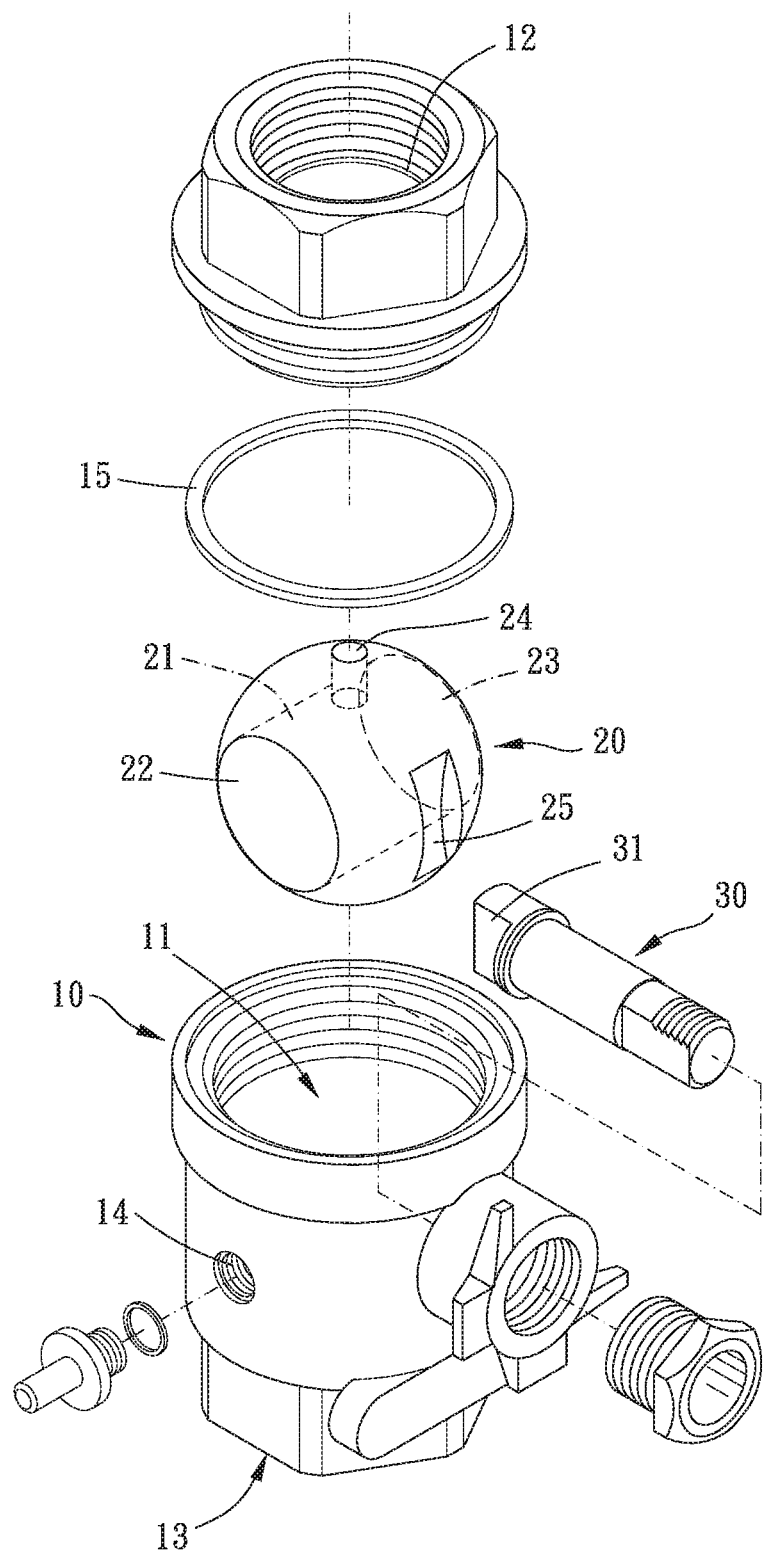
FIG. 2 is a breakdown drawing of a ball valve of the present invention.
Figure 3:
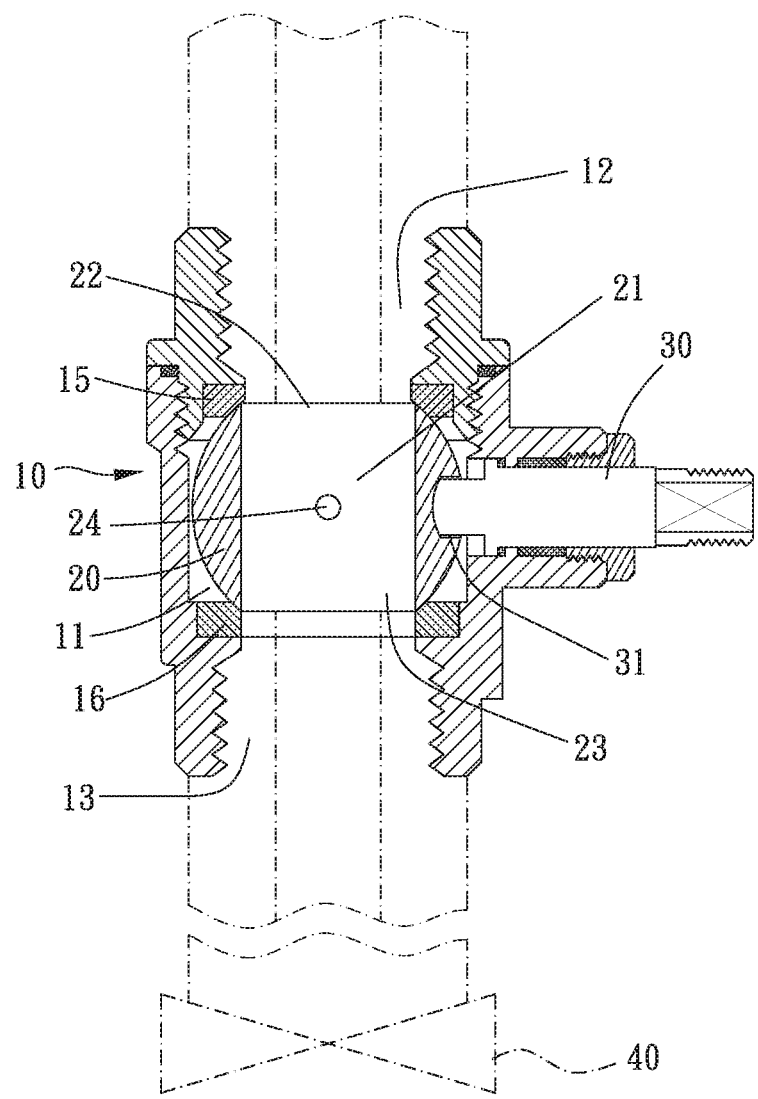
FIG. 3 is a profile of a ball valve of the present invention.
Figure 4:
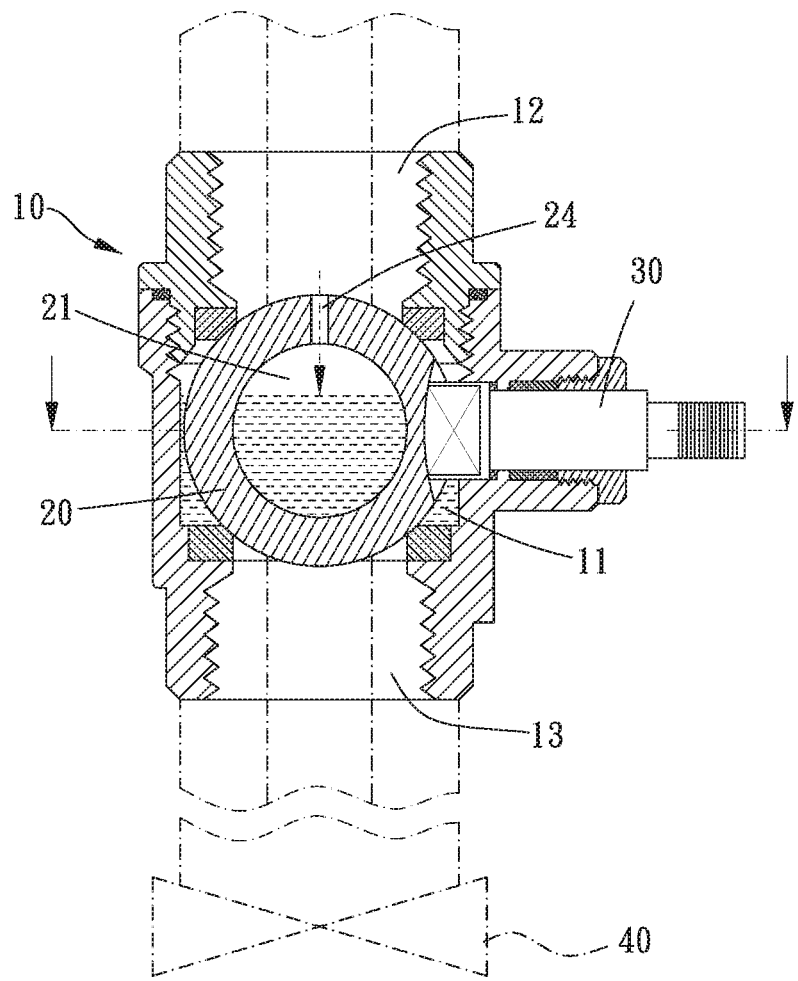
FIG. 4 is a profile of a ball valve of the present invention when a ball body is at a washing position.
Figure 5:
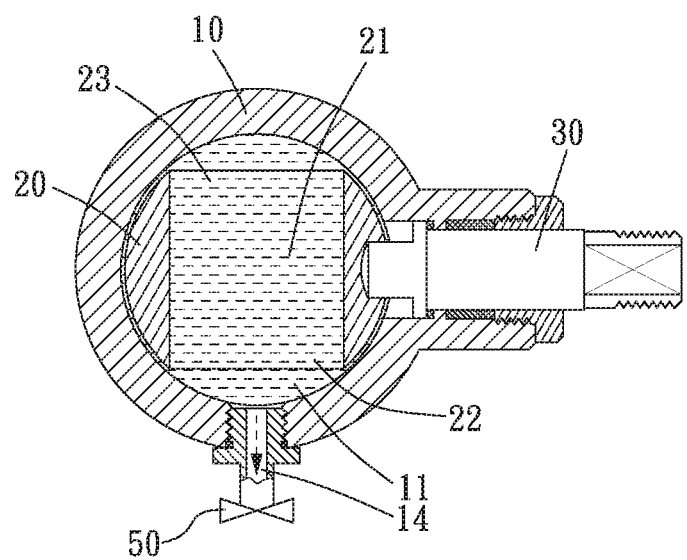
FIG. 5 is a profile of FIG. 4.

Please refer to FIG. 1 to FIG. 9, the ball valve 100 for fermentation tank of the present invention includes a main body 10, a ball body 20, and a rotation mechanism.

The main body 10 encloses a chamber 11 therein and has a first inlet 12 and a first outlet 13 at two ends thereof. The first inlet 12 and the first outlet communicate the chamber 11 respectively. The main body 10 further has a discharge port 14 at a lateral wall thereof. The discharge port 14 communicates the chamber 11 and is located between the first inlet 12 and the first outlet 13. A first valve 50 is disposed on the discharge valve 14. A second valve 40 is disposed on the first outlet 13. In the present embodiment, the main body includes a main member and a cover. The chamber and the first outlet is formed on the main member, and the first inlet is formed on the cover. The cover is screwed with the main member.

The ball body 20 is rotatable received in the chamber 11 of the main body 10. The ball body 20 is formed with a flow channel 21. A second inlet 22 and a second outlet 23 are formed at two ends of the flow channel 21 respectively. The ball body 20 further has a liquid intake port 24 communicating the flow channel 21. A gap is formed between the ball body 20 and an inner wall of the chamber 11.

The rotation mechanism is connected to the ball body 20 to rotate the ball body 20 between an opening position and a washing position. When the ball body 20 is located at the opening position, the second inlet 22 communicates the first inlet 12, the second outlet 23 communicates the first outlet 13, and the liquid intake port 24 faces the gap to communicate the gap. When the ball body 20 is located at the washing position, the second inlet 22 and the second outlet 23 both face the gap to communicate the gap respectively, and the liquid intake port 24 communicates the first inlet 12. In the present embodiment, the rotation mechanism 30 includes a pivoting bar 30. The pivoting bar 30 has an insertion portion 31 at an end thereof. The ball body 20 is formed with a recess 25 on an outer surface thereof. The insertion portion 31 penetrates the main body 10 to insert into the recess 25 so that the pivoting bar 30 is able to rotate the ball body 20.

In the present embodiment, when the ball body 20 is located at the washing position, one of the second inlet 22 and the second outlet 23 positionally corresponds to the discharge port 14 to make the flow channel 21 communicate the discharge port 14. The discharge port can be arranged at the extension line of the rotation axis of the ball body so that the second inlet, the second outlet, and the liquid intake port may not face the discharge port directly.

Besides, sealing rings 15,16 are disposed between the chamber 11 and the first inlet 12 and between the chamber 11 and the first outlet 13 so that the first inlet 12 and the second inlet 13 can only communicate the chamber 11 via the ball body 20.

Figure 6:
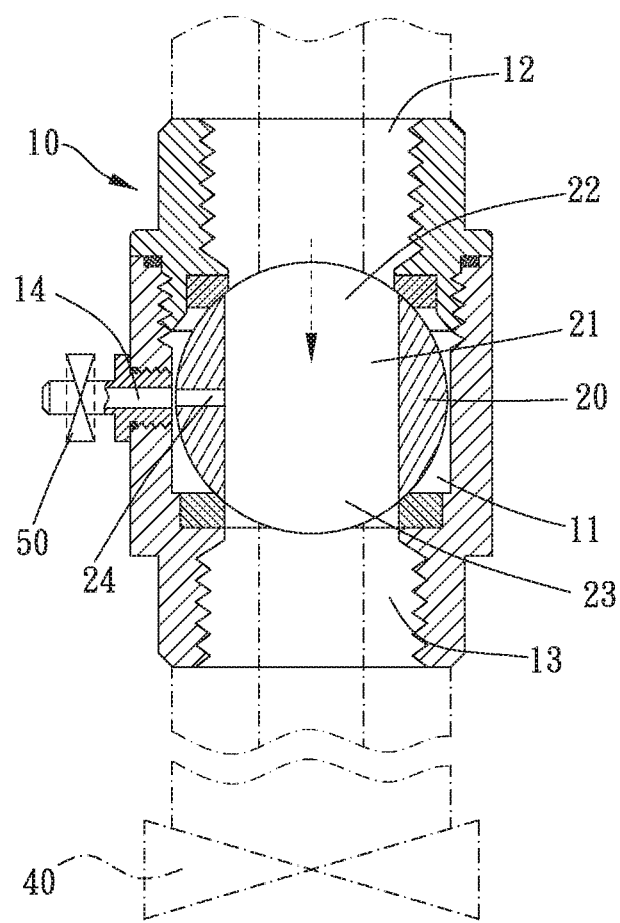
FIG. 6 to FIG. 8 are illustrations of a ball valve of the present invention.

In use, the ball body 20 is switched into the opening position, the second valve 40 is opened, and the first valve 50 is closed. Thereby, fermentation material can enter the flow channel 21 via the first inlet 12 and the second inlet 22, and leave from the second outlet 23 and the first outlet 13. Though the fermentation material may enter the gap, it may not flow out via the discharge port 14 because the first valve 50 is closed, as shown in FIG. 6.

Figure 7:
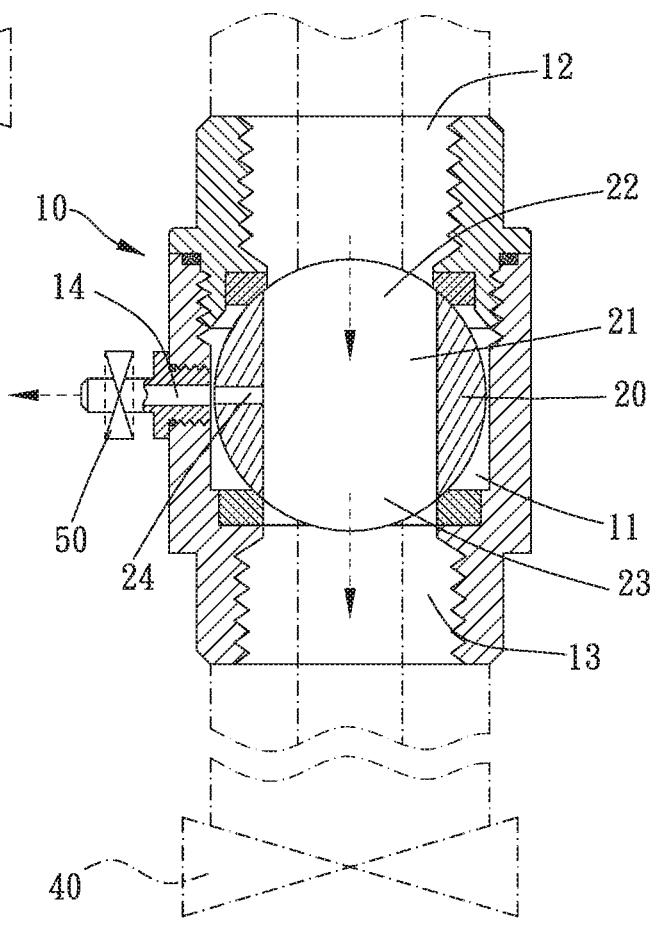
Figure 8:
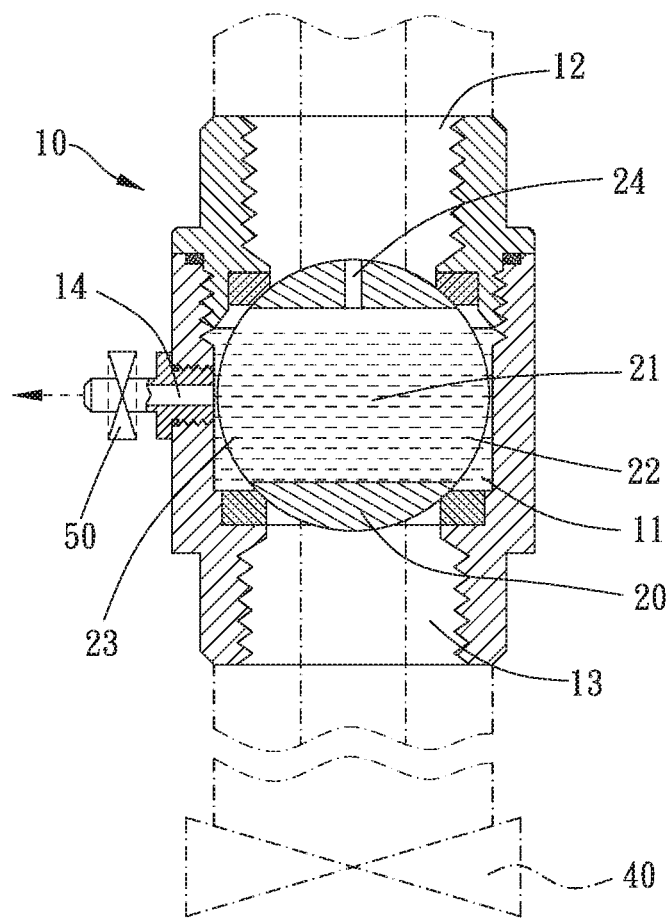
Figure 9:
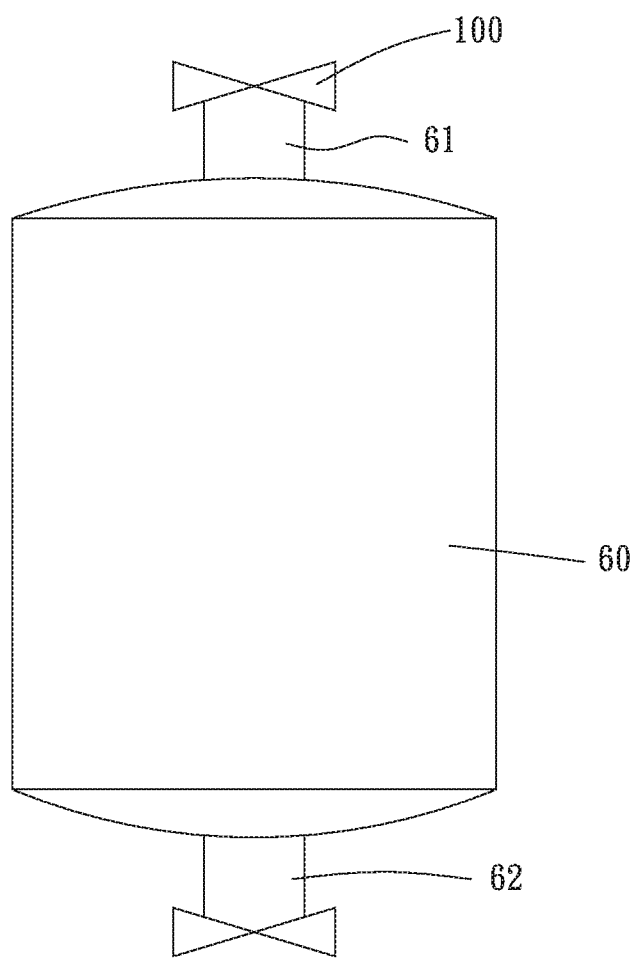
FIG. 9 is an illustration of a fermentation tank of the present invention.

The process of washing or disinfection includes two modes. First, the first valve 50 is opened, and the ball body 20 is at the opening position. And then, the washing fluid is injected into the ball valve via the first inlet 12 to wash both the gap and the fermentation tank connected to the first outlet 13. Preferably, the liquid intake port 24 extends in a direction vertical to the flow channel 21, which allows the washing fluid to fluently flow therethrough and have preferable flow rate and short flow distance so as to avoid deposition. The waste fluid produced by washing the gap can be discharged via the discharge port 14, as shown in FIG. 7. Second, to wash only the gap, the ball body 20 is switched into the washing position, the first valve 50 is kept opened. And then, the washing fluid enters the flow channel 21 via the liquid intake port 24 and further enters the gap via the second inlet 22 or the second outlet 23. The waste fluid can be discharged via the discharge port 14. Because the first outlet 13 is blocked by the ball body 20, the washing fluid may not flow through the first outlet 13 to contaminate the fermentation tank connected to the first outlet 13, as shown in FIG. 8.

After washing, the process of fermentation can re-start when the first valve 50 is closed, and the ball body 20 is switched into the opening position.

The present invention further provides a fermentation tank including the ball valve 100 mentioned above. Please refer to FIG. 9, the fermentation tank further includes a tank body 60. The tank body 60 has an inlet 61 and an outlet 62. The ball valve 100 is disposed on the inlet 61, and the first outlet is connected to the inlet 61.

In conclusion, the ball valve of the present invention can be washed without removing or detaching the ball valve, and the interior of the ball valve can be washed too. Thus, the fermentation product may not remain in the chamber to avoid breeding bacteria. Besides, the waste water after washing may not flow into the fermentation tank but be discharged via the discharge port. Thus, the fermentation tank may not be contaminated. On the other hand, the fermentation and the interior of the ball valve can be washed successively to ensure sanitary.

What is claimed is:

1. A ball valve for a fermentation tank, characterized by including:
   a main body, enclosing a chamber therein, the main body having a first inlet and a first outlet at two ends thereof, the first inlet and the first outlet communicating the chamber respectively, the main body having a discharge port on a lateral wall thereof, the discharge port communicating the chamber and being located between the first inlet and the first outlet, a first valve being disposed on the discharge port;
   a ball body, rotatably received in the chamber of the main body, the ball body being formed with a flow channel, two ends of the flow channel being a second inlet and a second outlet respectfully, the ball body further having a liquid intake port communicating the flow channel, a gap being formed between the ball body and an inner wall of the chamber;
   a rotation mechanism, connected to the ball body to make the ball body rotate between an open position and a washing position;
   when the ball body is located at the open position, the second inlet communicating the first inlet, the second outlet communicating the first outlet, the liquid intake port facing the gap to communicate the gap;
   when the ball body is located at the washing position, the second inlet and the second outlet both facing the gap, the liquid intake port communicating the first inlet;
   wherein the liquid intake port extends in a direction vertical to the flow channel.

2. The ball valve for the fermentation tank of claim 1, wherein a second valve is disposed on the first outlet.

3. The ball valve for the fermentation tank of claim 1, wherein when the ball body is located at the washing position, one of the second inlet and the second outlet positionally corresponds to the discharge port to make the flow channel communicate the discharge port.

4. The ball valve for the fermentation tank of claim 1, wherein the rotation mechanism includes a pivoting bar, the pivoting bar has an insertion portion at an end thereof, the ball body is formed with a recess at an outer surface, the insertion portion penetrates the main body to insert into the recess so that the pivoting bar is able to rotate the ball body.

5. The ball valve for the fermentation tank of claim 1, wherein sealing rings are disposed between the chamber and the first inlet and between the chamber and the first outlet respectively.

6. The ball valve for the fermentation tank of claim 1, wherein the fermentation tank further includes a tank body, the tank body has an inlet and an outlet, the ball valve for the fermentation tank is disposed on the inlet, the first inlet is connected to the inlet.

* * * * *